United States Patent [19]

Ericson

[11] Patent Number: 4,666,405
[45] Date of Patent: May 19, 1987

[54] METHOD AND APPARATUS FOR POLYMERISING LIGHT-HARDENING DENTAL FILLINGS OF CLASS II TYPE COMPOSITE MATERIAL

[76] Inventor: Dan V. Ericson, Rådmansgatan 5, S-21146 Malmo, Sweden

[21] Appl. No.: 582,470

[22] Filed: Feb. 22, 1984

[30] Foreign Application Priority Data

Feb. 21, 1983 [SE] Sweden ............................... 8300924

[51] Int. Cl.[4] ............................................... A61C 5/00
[52] U.S. Cl. .................................... 433/229; 433/215; 433/228.1
[58] Field of Search .................. 433/229, 215, 32, 29, 433/228

[56] References Cited

U.S. PATENT DOCUMENTS 3,868,513  2/1975  Gonser ................................ 433/228

Primary Examiner—Robert Peshock
Attorney, Agent, or Firm—Cushman, Darby & Cushman

[57] ABSTRACT

In a method of preparing a class II dental filling of a light-hardening filling material in a drilled-out tooth surrounded by a matrix band, the drilled-out tooth is filled with a light-hardening filling material in which the lower part of a light-transmitting adapter having a recess and attached to a light conductor, is pushed down into a filling material so that light is spread in the deeper parts of the filling, while at the same time the lower part of the adapter is pressed against the point of contact of the adjacent tooth while the filling is hardened so that satisfactory approximal contact is obtained.

A light-transmitting adapter comprises an upper part having a recess for receiving a light conductor and a conical lower part adapted to conduct light-hardening filling material down into a drilled-out tooth. The lower part of the adapter is pressed against a matrix band surrounding the tooth so that satisfactory approximal contact with the adjacent tooth is obtained, while at the same time the deeper parts of the filling are made accessible to light from the light conductor.

6 Claims, 3 Drawing Figures

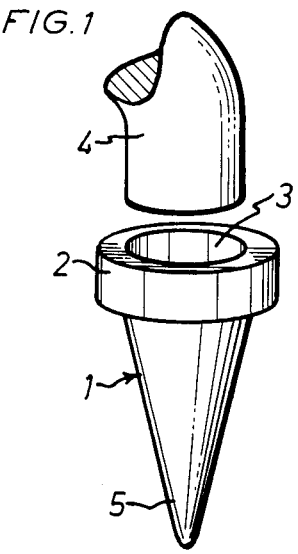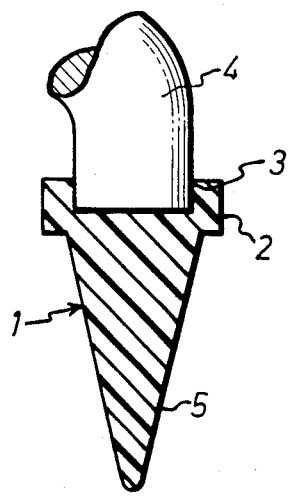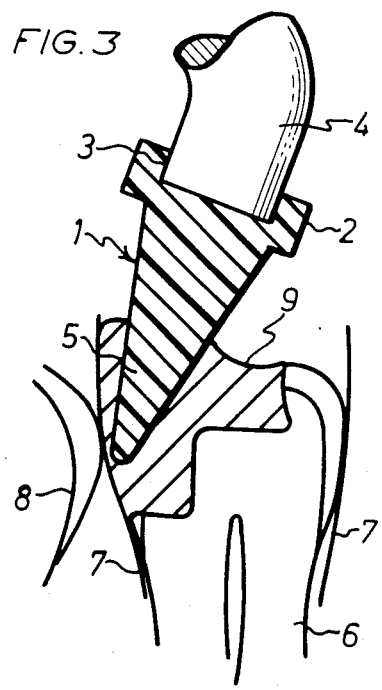

4,666,405

METHOD AND APPARATUS FOR POLYMERISING LIGHT-HARDENING DENTAL FILLINGS OF CLASS II TYPE COMPOSITE MATERIAL

The present invention relates to a light-transmitting adapter for mounting on a fibre optic handpiece for light-induced polymerisation of class II type dental fillings, such that the light-transmitting adapter is pressed into the filling material in the approximal cavity and, at the same time, is used for pressing the matrix band against the contact point of the adjacent tooth so that optimal approximal contact is obtained.

Filling materials where polymerisation is induced by illumination with ultraviolet light or intensely visible light, have become increasingly more common on the market. The problem encountered with these opaque filling materials is that it is difficult to polymerise the entire filling because the activating light has a restricted range within the material. Another problem encountered in preparing fillings of these materials (and other composite materials) of class II type in premolars and molars, lies in the difficulty of establishing optimal contact with the adjacent tooth, which is due to the fact that these materials cannot be made to condense like, for example, amalgam which causes a mechanical interlocking of alloy particles within the material. Thus, when amalgam is pressed into a cavity which is defined by a more or less resilient matrix band, the matrix band is unable to spring back and to deform the amalgam which retains the shape imparted to it during condensation, even though it is still plastic. A composite material, however, is deformed by the resiliency of the matrix band, resulting in an unsatisfactory contact.

If a composite material is to be used for class II type fillings, the matrix band must be pressed against the adjacent tooth while the material is being polymerised in order to establish adequate contact.

Technically, it is difficult to establish such a satisfactory contact when light-hardening materials are used because the dentist then must use both of his hands for handling the instruments. He is then obliged to press the matrix band against the adjacent tooth with one instrument, while at the same time polymerising the filling by means of the fiber optic handpiece or the like which he is holding in the other hand.

The main object of the present invention is to simplify the handling of light-activating filling materials, while at the same time illuminating a major part of the filling, especially its deeper portions, than when the above-mentioned technique is utilised, and to establish an optimal approximal contact point.

Due to its simple construction, the present invention can be produced in an inexpensive and simple manner in different types of plastics materials.

The invention will be described in greater detail below, reference being had to the accompanying drawings illustrating embodiments of the invention. In the drawings:

FIG. 1 illustrates a light-transmitting adapter 1 having in its upper part 2 a recess 3 in which a fiber optic handpiece 4 or the like may be inserted so that the adapter 1 is held firmly in position on the fiber optic handpiece 4 by friction or screwing, or the like.

FIG. 2 illustrates the adapter in cross section, the fibre optic handle 4 or the like being mounted in the recess 3. The upper part of the adapter merely constitutes an attachment for the fibre optic handpiece 4. The lower part 5 of the adapter is conical and sufficiently narrow to permit the insertion in a cavity. The lower part may also be shaped as a truncated cone or, alternatively, as a cone which is ellipsoidal in cross section or formed in some other manner so that it cannot be mechanically retained in a polymerised filling material.

FIG. 3 is a cross section of a tooth 6 surrounded by a matrix band 7 bordering on the adjacent tooth 8. In the tooth 6 which has been drilled out to accommodate a filling, a filling material 9 of the type described above has been inserted.

The lower part 5 of the adapter is pressed into the filling material 9 and, at the same time, against the matrix band 7 which is pressed against the adjacent tooth 8.

When light passes through the fiber optic handle 4 through the adapter 1, the light will induce polymerisation in those parts of the filling material 9 which are illuminated. Also deeper parts of the interior of the filling are illuminated in that the adapter is inserted in the filling material.

When the filling material has polymerised, the adapter is removed from the filling, and the hole left by the adapter is filled with fresh material, the filling again being illuminated.

What I claim and desire to secure by Letters Patent is:

1. An apparatus for preparing a dental filling of light-hardening filling material, said apparatus comprising a light conductor for illuminated a filling material placed within a tooth, wherein one end of said light conductor is pointed and adapted to be pushed into the filling material such that it engages with a matrix band placed around the tooth and urges said matrix band against the contact point of an adjacent tooth.

2. An apparatus as claimed in claim 1, wherein said said one end is a conical adapter for detachable mounting on said light conductor, at least the lower part of said conductor being formed of a light-transmitting material that cannot be bonded chemically to the filling material.

3. A method of preparing a dental filling of light-hardening filling material in a tooth, the drilled-out tooth being filled with a light-hardening filling material, wherein one end of a light conductor having its other end connected to a light source, is pushed into the filling material; and said light source is activated to harden the deeper parts of the filling.

4. A method as claimed in claim 3, wherein the said one end of the light conductor is pressed against a matrix band surrounding the tooth so that said matrix band in its turn is pressed against the adjacent tooth to provide for satisfactory approximal contact during hardening.

5. A method of preparing a dental filling of light-hardening filling material in a tooth, the drilled-out tooth being filled with a light-hardening filling material, wherein one end of a light conductor having its other end connected to a light source, is pushed into the filling material to transmit and spread light in the deeper parts of the filling and is pressed against a matrix band surrounding the tooth so that said matrix band in its turn is pressed against the adjacent tooth to provide for satisfactory approximal contact during hardening; and said light source is activated to harden the deeper parts of the filling.

6. A method of filling a drilled-out cavity in a tooth which is provided with a matrix band, said method comprising: filling the cavity with a light-hardening filling material; pressing into the filling the light-emitting point portion of a pointed light conductor, the other end of which is connected to a light source such that the point portion becomes surrounded by filling material and the point becomes engaged with the matrix band and presses the matrix band against an adjacent tooth and such that simultaneously light being emitted from the point portion is transmitted into the surrounding filling material to harden the deeper portions thereof; withdrawing the point portion from the filling material; filling the resulting hole in the filling material with additional filling material; and illuminating such additional material to harden the same.

* * * * *